(12) United States Patent
Prabhu

(10) Patent No.: US 11,166,818 B2
(45) Date of Patent: Nov. 9, 2021

(54) DEVICES FOR ADJUSTING THE CURVATURE OF CARDIAC VALVE STRUCTURES

(71) Applicant: Evalve, Inc., Santa Clara, CA (US)

(72) Inventor: Santosh V. Prabhu, Sunnyvale, CA (US)

(73) Assignee: EVALVE, INC., Santa Clara, CA (US)

( * ) Notice: Subject to any disclaimer, the term of this patent is extended or adjusted under 35 U.S.C. 154(b) by 224 days.

(21) Appl. No.: 16/420,882

(22) Filed: May 23, 2019

(65) Prior Publication Data

US 2019/0274831 A1 Sep. 12, 2019

Related U.S. Application Data

(63) Continuation of application No. 15/347,543, filed on Nov. 9, 2016, now Pat. No. 10,363,138.

(51) Int. Cl.
*A61F 2/24* (2006.01)

(52) U.S. Cl.
CPC .......... *A61F 2/2451* (2013.01); *A61F 2/2466* (2013.01); *A61F 2210/0004* (2013.01);
(Continued)

(58) Field of Classification Search
CPC ........ A61F 2/07; A61F 2/2442; A61F 2/2451; A61F 2/2466; A61F 2/2481; A61F 2/88;
(Continued)

(56) References Cited

U.S. PATENT DOCUMENTS

| 1,996,261 A | 4/1935 | Storz |
| 3,671,979 A | 6/1972 | Moulopoulos |

(Continued)

FOREIGN PATENT DOCUMENTS

| CN | 1469724 | 1/2004 |
| CN | 102770080 | 11/2012 |

(Continued)

OTHER PUBLICATIONS

Abe et al, De Vega's Annuloplasty for Acquired Tricuspid Disease: Early and Late Results in 110 Patients, Ann. Thorac. Surg., Jan. 1989, pp. 670-676, vol. 48.
(Continued)

*Primary Examiner* — Robert A Lynch
(74) *Attorney, Agent, or Firm* — Workman Nydegger

(57) ABSTRACT

An interventional curvature device for temporarily adjusting the structure of a heart during a heart valve repair procedure in order to enhance the effectiveness of the heart valve repair procedure. The curvature device is adjustable between a collapsed configuration with a profile suitable for delivery of the device to a coronary sinus and great cardiac vein of a patient, and an expanded configuration for lodging of the device at the coronary sinus and great cardiac vein. The curvature device has a distal section that anchors within the great cardiac vein, and a proximal section that anchors within the coronary sinus. A tether is coupled to the distal end of the device and extends through the device and past the proximal end. An increase in tension in the tether increases the curvature of the device.

17 Claims, 4 Drawing Sheets

(52) U.S. Cl.
CPC ............... *A61F 2210/0014* (2013.01); *A61F 2210/0061* (2013.01); *A61F 2230/0013* (2013.01); *A61F 2250/001* (2013.01); *A61F 2250/0004* (2013.01)

(58) Field of Classification Search
CPC ...... A61F 2/90; A61F 2/91; A61F 2002/2484; A61F 2210/0004; A61F 2210/0014; A61F 2210/0061; A61F 2017/00243
See application file for complete search history.

(56) References Cited

U.S. PATENT DOCUMENTS

| | | |
|---|---|---|
| 4,406,656 A | 9/1983 | Hattler et al. |
| 4,484,579 A | 11/1984 | Meno et al. |
| 4,510,934 A | 4/1985 | Batra |
| 4,578,061 A | 3/1986 | Lemelson |
| 4,686,965 A | 8/1987 | Bonnet et al. |
| 4,777,951 A | 10/1988 | Cribier et al. |
| 4,878,495 A | 11/1989 | Grayzel |
| 4,917,089 A | 4/1990 | Sideris |
| 4,969,890 A | 11/1990 | Sugita et al. |
| 4,994,077 A | 2/1991 | Dobben |
| 5,061,277 A | 10/1991 | Carpentier et al. |
| 5,078,722 A | 1/1992 | Stevens |
| 5,108,368 A | 4/1992 | Hammerslag et al. |
| 5,195,968 A | 3/1993 | Lundquist et al. |
| 5,201,757 A | 4/1993 | Heyn et al. |
| 5,251,611 A | 10/1993 | Zehel et al. |
| 5,271,381 A | 12/1993 | Ailinger et al. |
| 5,304,131 A | 4/1994 | Paskar |
| 5,306,286 A | 4/1994 | Stack et al. |
| 5,318,525 A | 6/1994 | West et al. |
| 5,325,845 A | 7/1994 | Adair |
| 5,332,402 A | 7/1994 | Teitelbaum |
| 5,359,994 A | 11/1994 | Kreuter et al. |
| 5,364,351 A | 11/1994 | Heinzelman et al. |
| 5,368,564 A | 11/1994 | Savage |
| 5,411,552 A | 5/1995 | Andersen et al. |
| 5,445,646 A | 8/1995 | Euteneuer et al. |
| 5,472,423 A | 12/1995 | Gronauer |
| 5,507,725 A | 4/1996 | Savage et al. |
| 5,507,757 A | 4/1996 | Sauer et al. |
| 5,527,321 A | 6/1996 | Hinchliffe |
| 5,554,185 A | 9/1996 | Block et al. |
| 5,571,085 A | 11/1996 | Accisano, III |
| 5,571,135 A | 11/1996 | Fraser et al. |
| 5,609,598 A | 3/1997 | Laufer et al. |
| 5,662,606 A | 9/1997 | Cimino et al. |
| 5,669,917 A | 9/1997 | Sauer et al. |
| 5,669,919 A | 9/1997 | Sanders et al. |
| 5,690,671 A | 11/1997 | McGurk et al. |
| 5,695,504 A | 12/1997 | Gifford, III et al. |
| 5,718,725 A | 2/1998 | Sterman et al. |
| 5,722,421 A | 3/1998 | Francese et al. |
| 5,749,828 A | 5/1998 | Solomon et al. |
| 5,769,812 A | 6/1998 | Stevens et al. |
| 5,772,578 A | 6/1998 | Heimberger et al. |
| 5,797,960 A | 8/1998 | Stevens et al. |
| 5,810,847 A | 9/1998 | Laufer et al. |
| 5,810,849 A | 9/1998 | Kontos |
| 5,810,876 A | 9/1998 | Kelleher |
| 5,814,029 A | 9/1998 | Hassett |
| 5,820,591 A | 10/1998 | Thompson et al. |
| 5,820,592 A | 10/1998 | Hammerslag |
| 5,823,955 A | 10/1998 | Kuck et al. |
| 5,823,956 A | 10/1998 | Roth et al. |
| 5,829,447 A | 11/1998 | Stevens et al. |
| 5,840,081 A | 11/1998 | Andersen et al. |
| 5,843,103 A | 12/1998 | Wulfman |
| 5,855,614 A | 1/1999 | Stevens et al. |
| 5,860,990 A | 1/1999 | Nobles et al. |
| 5,873,882 A | 2/1999 | Straub et al. |
| 5,876,399 A | 3/1999 | Chia et al. |
| 5,916,147 A | 6/1999 | Boury |
| 5,957,973 A | 9/1999 | Quiachon et al. |
| 5,989,280 A | 11/1999 | Euteneuer et al. |
| 6,056,769 A | 5/2000 | Epstein et al. |
| 6,168,617 B1 | 1/2001 | Blaeser et al. |
| 6,174,322 B1 | 1/2001 | Schneidt |
| 6,180,059 B1 | 1/2001 | Divino, Jr. et al. |
| 6,197,043 B1 | 3/2001 | Davidson |
| 6,306,133 B1 | 10/2001 | Tu et al. |
| 6,312,447 B1 | 11/2001 | Grimes |
| 6,332,893 B1 | 12/2001 | Mortier et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,517,550 B1 | 2/2003 | Konya et al. |
| 6,537,314 B2 | 3/2003 | Langberg et al. |
| 6,575,971 B2 | 6/2003 | Hauck et al. |
| 6,579,279 B1 | 6/2003 | Rabiner et al. |
| 6,616,684 B1 | 9/2003 | Vidlund et al. |
| 6,629,534 B1 | 10/2003 | Goar et al. |
| 6,656,221 B2 | 12/2003 | Taylor et al. |
| 6,685,648 B2 | 2/2004 | Flaherty et al. |
| 6,689,164 B1 | 2/2004 | Seguin |
| 6,701,929 B2 | 3/2004 | Hussein |
| 6,702,826 B2 | 3/2004 | Liddicoat et al. |
| 6,718,985 B2 | 4/2004 | Hlavka et al. |
| 6,726,716 B2 | 4/2004 | Marquez |
| 6,740,107 B2 | 5/2004 | Loeb et al. |
| 6,752,813 B2 | 6/2004 | Goldfarb et al. |
| 6,755,777 B2 | 6/2004 | Schweich et al. |
| 6,797,002 B2 | 9/2004 | Spence et al. |
| 6,875,224 B2 | 4/2005 | Grimes |
| 6,926,725 B2 | 8/2005 | Cooke et al. |
| 6,945,978 B1 | 9/2005 | Hyde |
| 7,226,467 B2 | 6/2007 | Lucatero et al. |
| 7,291,168 B2 | 11/2007 | Macoviak et al. |
| 7,464,712 B2 | 12/2008 | Oz et al. |
| 7,563,267 B2 | 7/2009 | Goldfarb et al. |
| 7,563,273 B2 | 7/2009 | Goldfarb et al. |
| 7,637,933 B2 | 12/2009 | Dwyer et al. |
| 7,666,204 B2 | 2/2010 | Thornton et al. |
| 8,070,799 B2 | 12/2011 | Righini et al. |
| 8,435,279 B2 | 5/2013 | Beyerlein et al. |
| 8,518,106 B2 | 8/2013 | Duffy et al. |
| 8,523,881 B2 | 9/2013 | Cabiri et al. |
| 9,011,513 B2 | 4/2015 | Bialas et al. |
| 9,326,875 B2 | 5/2016 | Shumer et al. |
| 10,363,138 B2 | 7/2019 | Prabhu |
| 10,426,616 B2 | 10/2019 | Prabhu |
| 2001/0002445 A1 | 5/2001 | Vesely |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013547 A1 | 1/2002 | Paskar |
| 2002/0013571 A1 | 1/2002 | Goldfarb et al. |
| 2002/0035361 A1 | 3/2002 | Houser et al. |
| 2002/0042651 A1 | 4/2002 | Liddicoat et al. |
| 2002/0055767 A1 | 5/2002 | Forde et al. |
| 2002/0055775 A1 | 5/2002 | Carpentier et al. |
| 2002/0058910 A1 | 5/2002 | Hermann et al. |
| 2002/0058951 A1 | 5/2002 | Fiedler |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0161378 A1 | 10/2002 | Downing |
| 2002/0169360 A1 | 11/2002 | Taylor et al. |
| 2002/0173811 A1 | 11/2002 | Tu et al. |
| 2002/0173841 A1 | 11/2002 | Ortiz et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0045778 A1 | 3/2003 | Ohline et al. |

(56) References Cited

U.S. PATENT DOCUMENTS

| | | |
|---|---|---|
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0199975 A1 | 10/2003 | Shlomo |
| 2003/0233038 A1 | 12/2003 | Hassett. |
| 2004/0002719 A1 | 1/2004 | Oz et al. |
| 2004/0003819 A1 | 1/2004 | St. Goar et al. |
| 2004/0015232 A1 | 1/2004 | Shu et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0116848 A1 | 6/2004 | Gardeski et al. |
| 2004/0122448 A1 | 6/2004 | Levine |
| 2004/0127849 A1 | 7/2004 | Kantor |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133192 A1 | 7/2004 | Houser et al. |
| 2004/0133220 A1 | 7/2004 | Lashinski et al. |
| 2004/0133232 A1 | 7/2004 | Rosenbluth et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0147826 A1 | 7/2004 | Peterson |
| 2004/0148021 A1 | 7/2004 | Cartledge et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004667 A1* | 1/2005 | Swinford .............. A61F 2/2451 623/2.36 |
| 2005/0004668 A1 | 1/2005 | Aklog et al. |
| 2005/0010240 A1* | 1/2005 | Mathis .................. A61F 2/2451 606/151 |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038383 A1 | 2/2005 | Kelley et al. |
| 2005/0038508 A1 | 2/2005 | Gabbay |
| 2005/0038509 A1 | 2/2005 | Ashe |
| 2005/0049698 A1 | 3/2005 | Bolling et al. |
| 2005/0055089 A1 | 3/2005 | Macoviak et al. |
| 2005/0060030 A1 | 3/2005 | Lashinski et al. |
| 2005/0070844 A1 | 3/2005 | Chow et al. |
| 2005/0085903 A1 | 4/2005 | Lau |
| 2005/0137451 A1* | 6/2005 | Gordon ................ A61F 2/2451 600/37 |
| 2005/0143809 A1 | 6/2005 | Salahieh et al. |
| 2005/0149014 A1 | 7/2005 | Hauck et al. |
| 2005/0182475 A1 | 8/2005 | Jen et al. |
| 2005/0197694 A1 | 9/2005 | Pai et al. |
| 2005/0197695 A1 | 9/2005 | Stacchino et al. |
| 2005/0228422 A1 | 10/2005 | Machold et al. |
| 2005/0228495 A1 | 10/2005 | Macoviak |
| 2005/0251001 A1 | 11/2005 | Hassett |
| 2005/0256452 A1 | 11/2005 | DeMarchi et al. |
| 2005/0267493 A1 | 12/2005 | Schreck et al. |
| 2005/0272975 A1 | 12/2005 | McWeeney et al. |
| 2005/0273160 A1 | 12/2005 | Lashinski et al. |
| 2005/0277874 A1 | 12/2005 | Selkee |
| 2005/0277876 A1 | 12/2005 | Hayden |
| 2006/0004247 A1 | 1/2006 | Kute et al. |
| 2006/0015003 A1 | 1/2006 | Moaddes et al. |
| 2006/0015179 A1 | 1/2006 | Bulman-Fleming et al. |
| 2006/0020327 A1 | 1/2006 | Lashinski et al. |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0074484 A1 | 4/2006 | Huber |
| 2006/0089671 A1 | 4/2006 | Goldfarb et al. |
| 2006/0089711 A1 | 4/2006 | Dolan |
| 2006/0135961 A1 | 6/2006 | Rosenman et al. |
| 2006/0195012 A1 | 8/2006 | Mortier et al. |
| 2006/0200221 A1 | 9/2006 | Malewicz |
| 2006/0229708 A1 | 10/2006 | Powell et al. |
| 2006/0252984 A1 | 11/2006 | Randert et al. |
| 2006/0252993 A1 | 11/2006 | Freed et al. |
| 2006/0271064 A1 | 11/2006 | Agnew |
| 2006/0276891 A1* | 12/2006 | Nieminen .............. A61F 2/2442 623/2.37 |
| 2007/0038293 A1 | 2/2007 | St. Goar et al. |
| 2007/0055289 A1 | 3/2007 | Scouten et al. |
| 2007/0060997 A1 | 3/2007 | Boer |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0156225 A1 | 7/2007 | George et al. |
| 2007/0197858 A1 | 8/2007 | Goldfarb et al. |
| 2007/0198082 A1 | 8/2007 | Kapadia et al. |
| 2007/0213812 A1 | 9/2007 | Webler et al. |
| 2007/0260225 A1 | 11/2007 | Sakakine et al. |
| 2007/0299424 A1 | 12/2007 | Cumming et al. |
| 2008/0039935 A1 | 2/2008 | Buch et al. |
| 2008/0051703 A1 | 2/2008 | Thornton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goer et al. |
| 2008/0171976 A1 | 7/2008 | Rios et al. |
| 2008/0183194 A1 | 7/2008 | Goldfarb et al. |
| 2008/0188850 A1 | 8/2008 | Mody et al. |
| 2008/0195126 A1 | 8/2008 | Solem |
| 2008/0294175 A1 | 11/2008 | Bardsley et al. |

(56) References Cited

U.S. PATENT DOCUMENTS

| | | |
|---|---|---|
| 2009/0036768 A1 | 2/2009 | Seehusen et al. |
| 2009/0099554 A1 | 4/2009 | Forster et al. |
| 2009/0156995 A1 | 6/2009 | Martin et al. |
| 2009/0157162 A1 | 6/2009 | Chow et al. |
| 2009/0163934 A1 | 6/2009 | Raschdorf, Jr. et al. |
| 2009/0163986 A1 | 6/2009 | Tieu et al. |
| 2009/0177266 A1 | 7/2009 | Powell et al. |
| 2009/0182200 A1 | 7/2009 | Golden et al. |
| 2009/0198322 A1 | 8/2009 | Deem et al. |
| 2009/0204005 A1 | 8/2009 | Keast et al. |
| 2009/0270858 A1 | 10/2009 | Hauck et al. |
| 2009/0276039 A1 | 11/2009 | Meretei |
| 2009/0281619 A1 | 11/2009 | Le et al. |
| 2009/0326567 A1 | 12/2009 | Goldfarb et al. |
| 2010/0016958 A1 | 1/2010 | St. Goer et al. |
| 2010/0022823 A1 | 1/2010 | Goldfarb et al. |
| 2010/0121437 A1 | 5/2010 | Subramanian et al. |
| 2010/0217261 A1 | 8/2010 | Watson |
| 2010/0262231 A1 | 10/2010 | Tuval et al. |
| 2010/0268204 A1 | 10/2010 | Tieu et al. |
| 2010/0298929 A1 | 11/2010 | Thornton et al. |
| 2010/0331776 A1 | 12/2010 | Salahieh et al. |
| 2012/0022640 A1 | 1/2012 | Gross et al. |
| 2012/0065464 A1 | 3/2012 | Ellis et al. |
| 2012/0150194 A1 | 6/2012 | Odermatt et al. |
| 2012/0172915 A1 | 7/2012 | Fifer et al. |
| 2012/0179184 A1 | 7/2012 | Orlov |
| 2012/0265222 A1 | 10/2012 | Gordin et al. |
| 2012/0316639 A1 | 12/2012 | Kleinschrodt |
| 2012/0330348 A1 | 12/2012 | Strauss et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0190772 A1 | 7/2013 | Doerr |
| 2013/0231735 A1 | 9/2013 | Deem et al. |
| 2013/0304181 A1 | 11/2013 | Green et al. |
| 2013/0304200 A1 | 11/2013 | McLean et al. |
| 2014/0039511 A1 | 2/2014 | Morris et al. |
| 2014/0148889 A1 | 5/2014 | Deshmukh et al. |
| 2014/0180124 A1 | 6/2014 | Whiseant et al. |
| 2014/0200649 A1 | 7/2014 | Essinger et al. |
| 2014/0276913 A1 | 9/2014 | Tah et al. |
| 2014/0277356 A1 | 9/2014 | Shumer et al. |
| 2014/0309661 A1 | 10/2014 | Sheps et al. |
| 2014/0309670 A1 | 10/2014 | Bakos et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2015/0005801 A1 | 1/2015 | Marquis et al. |
| 2015/0051698 A1 | 2/2015 | Ruyra Baliarda et al. |
| 2015/0094800 A1 | 4/2015 | Chawla |
| 2015/0112430 A1 | 4/2015 | Creaven et al. |
| 2015/0119981 A1 | 4/2015 | Khairkhahan et al. |
| 2015/0142100 A1 | 5/2015 | Morriss et al. |
| 2015/0230947 A1 | 8/2015 | Krieger et al. |
| 2015/0257877 A1 | 9/2015 | Hernandez |
| 2015/0272759 A1 | 10/2015 | Argentine |
| 2015/0306806 A1 | 10/2015 | Dando et al. |
| 2015/0366665 A1 | 12/2015 | Lombardi et al. |
| 2016/0015410 A1 | 1/2016 | Asirvatham et al. |
| 2016/0038280 A1 | 2/2016 | Morriss et al. |
| 2016/0045314 A1 | 2/2016 | Keren et al. |
| 2016/0051386 A1 | 2/2016 | Haarmann-Thiemann |
| 2016/0116056 A1 | 4/2016 | Geissler |
| 2016/0128767 A1 | 5/2016 | Azamian et al. |
| 2016/0174979 A1 | 6/2016 | Wei |
| 2017/0042678 A1 | 2/2017 | Ganesan et al. |
| 2017/0143330 A1 | 5/2017 | Basude et al. |
| 2018/0008268 A1 | 1/2018 | Khairkhahan |
| 2018/0028215 A1 | 2/2018 | Cohen |
| 2018/0036119 A1 | 2/2018 | Wei et al. |
| 2018/0092661 A1 | 4/2018 | Prabhu |
| 2018/0161159 A1 | 6/2018 | Lee et al. |
| 2018/0360457 A1 | 12/2018 | Ellis et al. |
| 2019/0365536 A1 | 12/2019 | Prabhu |

FOREIGN PATENT DOCUMENTS

| | | |
|---|---|---|
| CN | 103841899 | 6/2014 |
| DE | 3504292 | 7/1986 |
| EP | 0179562 | 7/1989 |
| EP | 0782836 | 7/1997 |
| EP | 1674040 | 6/2006 |
| EP | 1935377 | 6/2008 |
| EP | 1980288 | 10/2008 |
| EP | 2005912 | 12/2008 |
| EP | 2537487 | 12/2012 |
| EP | 2641570 | 9/2013 |
| EP | 2702965 | 3/2014 |
| EP | 3009103 | 4/2016 |
| FR | 2768324 | 3/1999 |
| GB | 1598111 | 9/1981 |
| GB | 2151142 | 7/1985 |
| JP | H09253030 | 9/1997 |
| JP | 2006528911 | 12/2006 |
| JP | 2013516244 | 5/2013 |
| JP | 2014523274 | 9/2014 |
| WO | WO1991001689 | 2/1991 |
| WO | WO1992012690 | 8/1992 |
| WO | WO1994018881 | 9/1994 |
| WO | WO1994018893 | 9/1994 |
| WO | WO1995015715 | 6/1995 |
| WO | WO1996014032 | 5/1996 |
| WO | WO1996020655 | 7/1996 |
| WO | WO1997018746 | 5/1997 |
| WO | WO1997038748 | 10/1997 |
| WO | WO1997039688 | 10/1997 |
| WO | WO1997048436 | 12/1997 |
| WO | WO1998032382 | 7/1998 |
| WO | WO1998035638 | 8/1998 |
| WO | 99/01377 A1 | 1/1999 |
| WO | WO1999000059 | 1/1999 |
| WO | WO1999013777 | 3/1999 |
| WO | WO1999044524 | 9/1999 |
| WO | WO2000003651 | 1/2000 |
| WO | WO2000003759 | 1/2000 |
| WO | WO2000012168 | 3/2000 |
| WO | WO2000044313 | 8/2000 |
| WO | WO2000060995 | 10/2000 |
| WO | WO2001000111 | 1/2001 |
| WO | WO2001000114 | 1/2001 |
| WO | WO2001026557 | 4/2001 |
| WO | WO2001026586 | 4/2001 |
| WO | WO2001026588 | 4/2001 |
| WO | WO2001028455 | 4/2001 |
| WO | WO2001047438 | 7/2001 |
| WO | WO2001049213 | 7/2001 |
| WO | WO2001050985 | 7/2001 |
| WO | WO2001054618 | 8/2001 |
| WO | WO2001056512 | 8/2001 |
| WO | WO2001070320 | 9/2001 |
| WO | WO2001089440 | 11/2001 |
| WO | WO2001095831 | 12/2001 |
| WO | WO2001095832 | 12/2001 |
| WO | WO2001097741 | 12/2001 |
| WO | WO2002000099 | 1/2002 |
| WO | WO2002001999 | 1/2002 |
| WO | WO2002003892 | 1/2002 |
| WO | WO2002054167 | 5/2002 |
| WO | WO2002060352 | 8/2002 |
| WO | WO2002062263 | 8/2002 |
| WO | WO2002062270 | 8/2002 |
| WO | WO2002062408 | 8/2002 |
| WO | WO2003001893 | 1/2003 |
| WO | WO2003003930 | 1/2003 |
| WO | WO2003020179 | 3/2003 |
| WO | WO2003028558 | 4/2003 |
| WO | WO2003037171 | 5/2003 |
| WO | WO2003047467 | 6/2003 |
| WO | WO2003049619 | 6/2003 |
| WO | WO2003073913 | 9/2003 |
| WO | WO2003094801 | 11/2003 |
| WO | WO2003105667 | 12/2003 |
| WO | WO2004004607 | 1/2004 |
| WO | WO2004006810 | 1/2004 |

(56) References Cited

FOREIGN PATENT DOCUMENTS

| | | |
|---|---|---|
| WO | WO2004012583 | 2/2004 |
| WO | WO2004014282 | 2/2004 |
| WO | WO2004019811 | 3/2004 |
| WO | WO2004030570 | 4/2004 |
| WO | WO2004037317 | 5/2004 |
| WO | WO2004045370 | 6/2004 |
| WO | WO2004045378 | 6/2004 |
| WO | WO2004045463 | 6/2004 |
| WO | WO2004047679 | 6/2004 |
| WO | WO2004082523 | 9/2004 |
| WO | WO2004082538 | 9/2004 |
| WO | WO2004093730 | 11/2004 |
| WO | WO2004103162 | 12/2004 |
| WO | WO2004112585 | 12/2004 |
| WO | WO2004112651 | 12/2004 |
| WO | WO2005002424 | 1/2005 |
| WO | WO2005018507 | 3/2005 |
| WO | WO2005027797 | 3/2005 |
| WO | WO2005032421 | 4/2005 |
| WO | WO2005062931 | 7/2005 |
| WO | WO2005112792 | 12/2005 |
| WO | WO2006037073 | 4/2006 |
| WO | WO2006105008 | 10/2006 |
| WO | WO2006105009 | 10/2006 |
| WO | WO2006113906 | 10/2006 |
| WO | WO2006115875 | 11/2006 |
| WO | WO2006115876 | 11/2006 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2011102968 | 8/2011 |
| WO | WO 2012020521 | 2/2012 |
| WO | WO 2012151396 | 11/2012 |
| WO | WO2013049734 | 4/2013 |
| WO | WO2013103934 | 7/2013 |
| WO | WO 2014064694 | 5/2014 |
| WO | WO 2014121280 | 8/2014 |
| WO | 2015/020971 A1 | 2/2015 |
| WO | WO 2016022797 | 2/2016 |
| WO | WO 2016144708 | 9/2016 |
| WO | WO 2016150806 | 9/2016 |
| WO | WO2018026445 | 2/2018 |
| WO | WO2018089617 | 5/2018 |
| WO | WO2018094042 | 5/2018 |

OTHER PUBLICATIONS

Agricola et al., "Mitral Valve Reserve in Double Orifice Technique: an Exercise Echocardiographic Study," Journal of Heart Valve Disease, 11 (5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The edge to edge technique," The European Association for Cardio-Thoracic Surgery 14th Annual Meeting, Oct. 7-11, 2000, Book of Proceedings.
Ali Khan et al, Blade Atrial Septostomy: Experience with the First 50 Procedures, Cathet. Cardiovasc. Diagn., Aug. 1991, pp. 257-262, vol. 23.
Alvarez et al, Repairing the Degenerative Mitral Valve: Ten to Fifteen-year Follow-up, Journal of Thoracic Cardiovascular Surgery, Aug. 1996, pp. 238-247, vol. 112, No. 2.
Bach et al, Early Improvement in Congestive Heart Failure After Correction of Secondary Mitral Regurgitation in End-stage Cardiomyopathy, American Heart Journal, Jun. 1995, pp. 1165-1170, vol. 129, No. 6.
Bach et al, Improvement Following Correction of Secondary Mitral Regurgitation in End-stage Cardiomyopathy With Mitral Annuloplasty, Am. J. Cardiol., Oct. 15, 1996, pp. 966-969, vol. 78.

Bailey, "Mitral Regurgitation" in Surgery of the Heart, Chapter 20, pp. 686-737 (1955).
Bernal et al., "The Valve Racket': a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Chinese Office Action issued in Chinese Application No. 200980158707.2 dated Sep. 9, 2013.
Communication dated Apr. 28, 2017 issued by the European Patent Office in counterpart application No. 16196023.2.
Communication dated Jan. 26, 2017, from the European Patent Office in counterpart European application No. 16196023.2.
Extended European Search Report, dated Oct. 17, 2014, issued in European Patent Application No. 06751584.1.
Izzat et al., "Early Experience with Partial Left Ventriculectomy in the Asia-Pacific Region," Annuals of Thoracic Surgery, 67:1703-1707 (1999).
Kameda et al., Annuloplasty for Severe Mitral Regurgitation Due to Dilated Cardiomyopathy, Ann. Thorac. Surg., 1996, pp. 1829-1832, vol. 61.
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Maisano et al., "The double orifice repair for Barlow Disease: a simple solution for a complex repair," Supplement I Circulation, (Nov. 1999); 100(18): 1-94.
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., Tricuspid Valve Repair with the Cosgrove-Edwards Annuloplasty System, Ann. Thorac. Surg., Jan. 16, 1997, pp. 267-268, vol. 64.
Moainie et al., "Correction of Traumatic Tricuspid Regurgitation Using the Double Orifice Technique," Annals of Thoracic Surgery, 73:963-965 (2002).
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Patel et al., #57 Epicardial Atrial Defibrillation: Novel Treatment of Postoperative Atrial Fibrillation, 2003 STS Presentation, [Abstract Only].
Reul et al., "Mitral Valve Reconstruction for Mitral Insufficiency," Progress in Cardiovascular Diseases, XXXIX(6):567-599 (1997).
Ricchi et al, Linear Segmental Annuloplasty for Mitral Valve Repair, Ann. Thorac. Surg., Jan. 7, 1997, pp. 1805-1806, vol. 63.
Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Takizawa H et al.: "Development of a microfine active bending catheter equipped with MIF tactile sensors", Micro Electro Mechanical Systems, 1999. MEMS '99. Twelfth IEEE Interna tional Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3 figures 1-3.
Tamura et al., "Edge to Edge Repair for Mitral Regurgitation in a Patient with Chronic Hemodialysis: Report of A Case," Kyobu Geka. The Japanese Journal of Thoracic Surgery, 54(9):788-790 (2001).

(56) References Cited

OTHER PUBLICATIONS

Tibayan et al., #59 Annular Geometric Remodeling in Chronic Ischemic Mitral Regurgitation, 2003 STS Presentation, [Abstract Only].
Uchida et al, Percutaneous Cardiomyotomy and Valvulotomy with Angioscopic Guidance, Am. Heart J., Apr. 1991, pp. 1221-1224, vol. 121.
Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
U.S. Appl. No. 14/216,813, filed Mar. 9, 2017, Office Action.
U.S. Appl. No. 14/216,813, filed Dec. 15, 2017, Office Action.
U.S. Appl. No. 14/216,813, filed Apr. 6, 2018, Office Action.
U.S. Appl. No. 14/216,813, filed Jan. 31, 2019, Office Action.
U.S. Appl. No. 14/577,852, filed Oct. 20, 2016, Office Action.
U.S. Appl. No. 14/577,852, filed May 16, 2017, Office Action.
U.S. Appl. No. 14/577,852, filed Sep. 7, 2017, Office Action.
U.S. Appl. No. 14/577,852, filed Apr. 25, 2018, Notice of Allowance.
U.S. Appl. No. 15/347,543, filed Dec. 28, 2018, Office Action.
U.S. Appl. No. 15/347,543, filed Mar. 18, 2019, Notice of Allowance.
U.S. Appl. No. 15/354,644, filed Nov. 5, 2018, Office Action.
U.S. Appl. No. 15/354,644, filed Feb. 28, 2019, Office Action.
U.S. Appl. No. 15/354,644, filed May 22, 2019, Notice of Allowance.
Abe et al., "Updated in 1996—De Vega's Annuloplasty for Acquired Tricuspid Disease: Early and Late Results in 110 Patients", Ann. Thorac. Surg., pp. 1876-1877, vol. 62 (1996).
Bhudia et al., "Edge-to-edge Mitral Repair: A Versatile Mitral Repair," http://wvvw.sts.org/doc/7007 accessed on Sep. 24, 2008.

\* cited by examiner

DEVICES FOR ADJUSTING THE CURVATURE OF CARDIAC VALVE STRUCTURES

CROSS-REFERENCE TO RELATED APPLICATIONS

This is a continuation application of U.S. patent application Ser. No. 15/347,543, filed Nov. 9, 2016, the disclosure of which is incorporated herein by this reference.

BACKGROUND

The mitral valve controls blood flow from the left atrium to the left ventricle of the heart, preventing blood from flowing backwards from the left ventricle into the left atrium so that it is instead forced through the aortic valve for delivery of oxygenated blood throughout the body. A properly functioning mitral valve opens and closes to enable blood flow in one direction. However, in some circumstances the mitral valve is unable to close properly, allowing blood to regurgitate back into the atrium. Such regurgitation can result in shortness of breath, fatigue, heart arrhythmias, and even heart failure.

Mitral valve regurgitation has several causes. Functional mitral valve regurgitation (FMR) is characterized by structurally normal mitral valve leaflets that are nevertheless unable to properly coapt with one another and close properly due to other structural deformations of surrounding heart structures. Other causes of mitral valve regurgitation are related to defects of the mitral valve leaflets, mitral valve annulus, or other mitral valve tissues. In some circumstances, mitral valve regurgitation is a result of endocarditis, blunt chest trauma, rheumatic fever, Marfan syndrome, carcinoid syndrome, or congenital defects to the structure of the heart. Other cardiac valves, in particular the tricuspid valve, can similarly fail to properly close, resulting in undesirable regurgitation.

Heart valve regurgitation is often treated by replacing the faulty valve with a replacement valve implant or by repairing the valve through an interventional procedure. One method for repairing the regurgitant mitral valve is by delivering and deploying an interventional clip at the heart valve. Typically, the clip is deployed so as to grip the anterior and posterior leaflets of the valve. The clip thereby functions to bring the gripped leaflets closer to one another to reduce the space through which regurgitant flows can pass so that the valve can more effectively close. However, difficulties can arise related to positioning and deployment of the clip device. Often, it is difficult to properly grasp the targeted leaflets with the clip device. In particular, the leaflets of a regurgitant mitral valve are typically already malformed or overly spaced from one another, making it difficult to manipulate the clip device so as to properly grasp and maintain hold of both leaflets.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein are directed to devices and methods for temporarily manipulating the structure of the mitral valve during a mitral valve treatment procedure, such as a mitral valve repair or replacement procedure. In some embodiments, a retrievable curvature device is deployed so as move and/or maintain the leaflets of the mitral valve closer to one another. With the leaflets moved and/or maintained in a relatively closer position, a leaflet approximation procedure, such as the deployment and implantation of a leaflet-grasping clip, is able to proceed with more effective grasping and approximating of the leaflet tissue.

In some embodiments, the retrievable curvature device is delivered (e.g., through a transcatheter approach) to the coronary sinus (CS) and at least an adjacent portion of the great cardiac vein (GCV) of the patient. The curvature device is configured to temporarily lodge within the CS and GCV. Actuation of the curvature device causes the device to increase in curvature, which in turn increases the curvature of the CS and GCV in which the device is temporarily lodged. An increase in the curvature of the CS and GCV affects the structure of the mitral valve annulus, and functions to move the leaflets of the mitral valve annulus closer to one another and/or to maintain the leaflets close to one another.

In some embodiments, a curvature device is moveable between a collapsed configuration having a profile suitable for delivery of the device to a CS and GCV of a patient and an expanded configuration having a profile suitable for lodging of the device at the CS and GCV. The curvature device includes a distal end section having a distal anchor configured to anchor within the GCV when the device is deployed to the expanded position at the GCV, and a proximal end section having a proximal anchor configured to anchor within the CS when the device is deployed to the expanded configuration at the CS. The curvature device also includes a tether coupled to the distal end section and extending through and past the proximal end section. The tether is tensionable such that an increase in tension increases the curvature of the device and a decrease in tension lessens the curvature of the device.

In some embodiments, the curvature device is at least partially formed from a shape memory material that enables the device to self-expand to the expanded configuration when not constrained to the collapsed configuration. In some embodiments, the curvature device is at least partially formed as a balloon structure capable of being filled with a fluid to move toward the expanded configuration and withdrawn of fluid to move toward the collapsed configuration.

In some embodiments, a retrievable curvature device is included as part of an interventional system. The interventional system includes a delivery catheter having a proximal end and a distal end, and including a sheath at the distal end configured to house the curvature device to maintain the curvature device in the collapsed configuration while the curvature device is housed within the sheath. The interventional system also includes a handle coupled to the proximal end of the delivery catheter, the tether extending to the handle, the handle including a control operatively coupled to the tether to enable adjusting of tension in the tether through actuation of the control. In some embodiments, the interventional system also includes one or more control lines extending from the handle to the distal end of the delivery catheter such that tensioning of the one or more control lines acts to bend the distal end of the delivery catheter to provide steering functionality to the delivery catheter. In some embodiments, the handle also houses or otherwise includes a mechanism for proximally retracting the sheath or distally pushing the implant out.

Certain embodiments disclosed herein are directed to methods for temporarily adjusting the structure of a heart to enable more effective treatment of the heart. In some embodiments, a method includes delivering a curvature device to a coronary sinus and great cardiac vein of the heart, deploying the curvature device such that a distal end section of the curvature device lodges within the GCV and such that a proximal end section of the curvature device lodges within the CS, and tensioning a tether of the curvature device, the tether being coupled to the distal end section and passing through the proximal end section such that the tensioning causes the distal end section to bend toward the proximal end section to increase the curvature of the curvature device.

In some embodiments, the curvature device is delivered using a transjugular or transfemoral approach. In some embodiments, the method further includes releasing tension in the tether to lessen the curvature of the curvature device, and removing the curvature device from the GCV and the CS.

In some embodiments, the heart treatment procedure is a mitral valve repair procedure, such as a mitral valve leaflet approximation procedure involving the placement of a leaflet-grasping clip at the mitral valve. In certain embodiments, the mitral valve repair procedure is carried out while the curvature device is tensioned to enhance the curvature of the device and to bring the leaflets of the mitral valve closer to one another.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Certain embodiments described herein are directed to devices and methods for enhancing the effectiveness of a mitral valve repair procedure by temporarily manipulating the structure of the mitral valve during deployment of a mitral valve repair device. In some embodiments, a curvature device is delivered to the coronary sinus (CS) and at least an adjacent portion of the great cardiac vein (GCV) of a patient. The curvature device is configured to temporarily lodge within the CS and GCV. Actuation of the curvature device causes the device to increase in curvature, which in turn increases the curvature of the CS and GCV in which the device is temporarily lodged. An increase in the curvature of the CS and GCV affects the structure of the mitral valve annulus, and functions to move the leaflets of the mitral valve annulus closer to one another and/or to maintain the leaflets close to one another. With the mitral valve annulus in a relatively more structurally constrained position as a result of deployment of the retrievable device, the leaflets of the mitral valve are brought closer to one another, enabling mitral valve repair procedures to proceed more effectively and efficiently.

Although many of the exemplary embodiments described herein are described in the context of constraining the mitral valve annulus during a clip placement procedure, it will be understood that similar principles may be applied to other implementations in which other interventional devices are deployed at the mitral valve and/or in which other repair procedures are performed. For example, one or more of the devices and methods described herein may be utilized in an annuloplasty procedure to aid in constraining and supporting the mitral valve annulus at a desired size and shape as the annuloplasty procedure is carried out. In another example, in some circumstances it may be desirable to utilize one or more of the embodiments described herein to adjust or support the mitral valve annulus during a replacement valve implant procedure, such as to enhance the fit of the replacement valve with the surrounding anatomical structures near the implant site. The features, components, and principles described herein may therefore be utilized in any procedure in which it is desirable to adjust or support the structure of the mitral valve annulus while the procedure is carried out.

Figure 1:
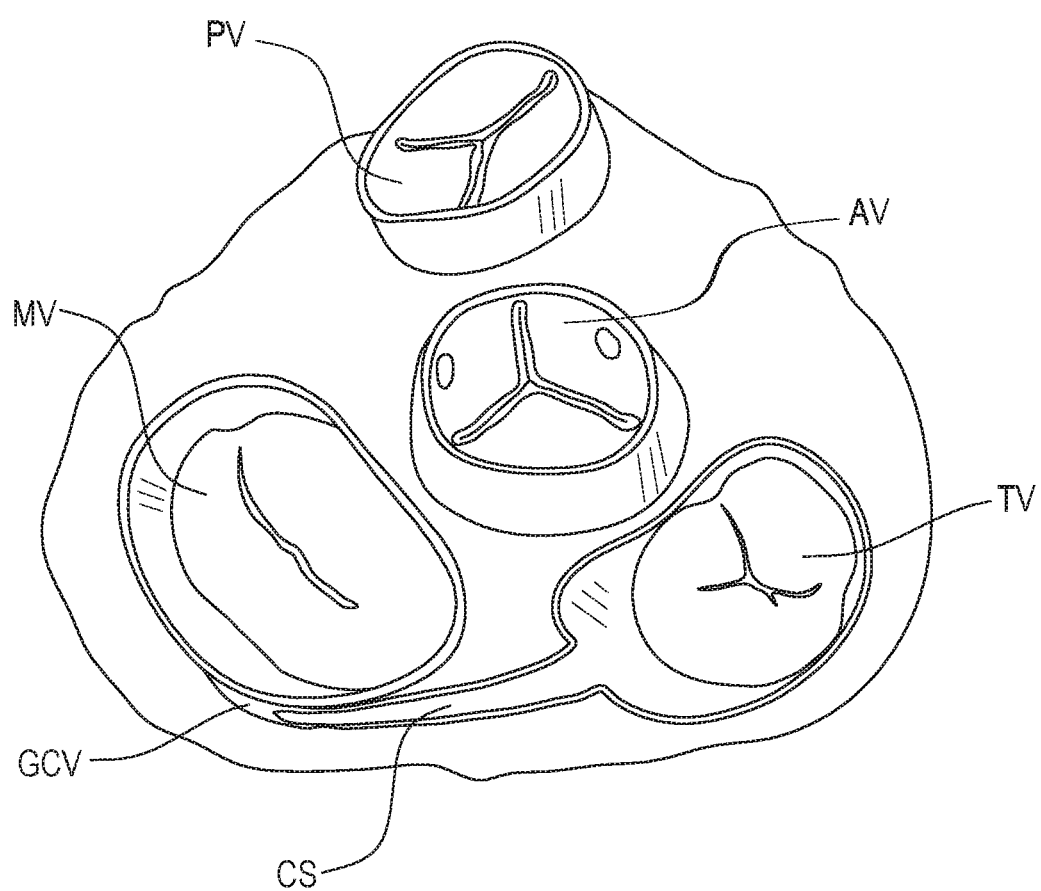
FIG. 1 illustrates a superior view of a human heart showing the mitral valve and other cardiac structures as viewed from the atrial side, and showing in particular the positions of the great cardiac vein (GCV) and coronary sinus (CS) relative to the mitral valve.

FIG. 1 illustrates a schematic of a human heart showing a cross-sectional view of the mitral valve ("MV") and other valves (tricuspid valve ("TV"), pulmonary valve ("PV"), aortic valve ("AV")) and structures as viewed from the atrial side of the heart. As shown, the CS and a portion of the GCV run along the left atrioventricular groove behind the posterior leaflet of the mitral valve. The CS joins the GCV with several other cardiac veins and forms a large vein that delivers the deoxygenated blood gathered from the myocardium into the right atrium, where it joins other deoxygenated blood gathered from throughout the body. As illustrated in FIG. 1, the CS and the GCV are positioned in the same structural vicinity as the mitral valve. In addition, the CS and adjacent portions of the GCV lie substantially within the same plane as the mitral valve annulus.

As explained in more detail below, this structural relationship enables the size and shape of the mitral valve annulus to be manipulated by adjusting the curvature of the portions of the CS and GCV that are structurally associated with the mitral valve annulus. For example, an increase to the curvature of these anatomical structures, so that they curve even more toward the mitral valve, will function to bring the posterior leaflet closer to the anterior leaflet. In contrast, a decrease to the curvature of these anatomical structures, so that they curve less toward the mitral valve, will function to pull the posterior leaflet further from anterior leaflet.

The exemplary embodiments described herein may be utilized to bring the mitral valve leaflets closer together by increasing the curvatures of the CS and GCV. Typically, bringing the leaflets closer together is desirable in order to increase the effectiveness of a concurrent mitral valve repair procedure, such as by making it easier to properly grasp each leaflet of the mitral valve using a clip device. However, it will be understood that, should it be clinically desired, one or more of the embodiments described herein may also be utilized to decrease the curvature of the CS and GCV and thereby increase the distance between the posterior and anterior leaflets.

Figure 2A:
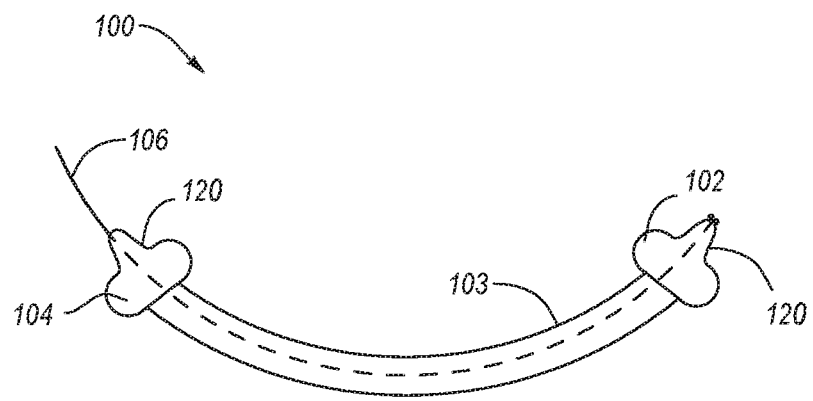
FIGS. 2A and 2B illustrate an exemplary curvature device that may be utilized to adjust the structure of a heart to enable more effective treatment of a mitral valve.
Figure 2B:
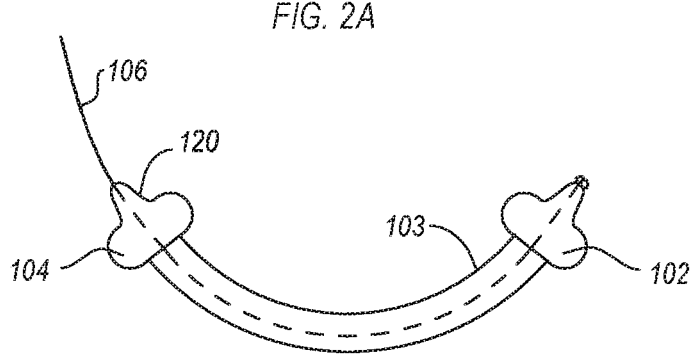

FIGS. 2A and 2B illustrate an embodiment of a curvature device 100 shown in a deployed/expanded position such as it would be when deployed within the CS and GCV, with FIG. 2B showing the device with an increased curvature relative to FIG. 2A. The illustrated curvature device 100 includes a distal anchor 102 at a distal end of the device and a proximal anchor 104 at a proximal end of the device. In this embodiment, a tether 106 is attached at or near the distal anchor 102 and extends from the distal anchor 102 through a body 103 and through and past the proximal anchor 104. In FIG. 2B, the tether 106 has greater tension than in FIG. 2A. As shown, by increasing the tension in the tether 106, the curvature of the device 100 is increased. In some embodiments, in addition to or as an alternative to changing the curvature, the circumference of the curvature device 100 can also reduce. Such reduction also contributes to reducing annular dimensions and bringing the leaflets closer to one another. For example, some embodiments may be configured with a length that can shorten to correspondingly reduce a circumference.

In some embodiments, the curvature device 100 has a precurved structure such that the device 100 is curved when deployed and when in a neutral configuration (e.g., in the absence of any tension applied by the tether 106). The precurvature can aid in properly seating the curvature device 100 within the GCV and CS of the patient before applying tension to increase the curvature of the device. For example, the precurvature can be generally matched to the average curvature of the GCV and CS of a typical patient.

In the illustrated embodiment, the tether 106 is attached at or near the distal anchor 102 and passes through the proximal anchor 104 without being anchored to the proximal anchor 104. This configuration allows the anchors to be pulled together upon the application of sufficient tension to the tether 106. The tether 106 may be coupled to the distal anchor 102 via one or more adhesives and/or mechanical fasteners, for example, or may be integrally attached to the distal anchor 102. In some embodiments, the proximal anchor 104 includes an aperture through which the tether 106 may pass to allow tensioning adjustments.

In some embodiments, the tether 106 may be passed through the proximal anchor 104 in either direction, to allow increasing and decreasing of the tension of the tether 106. Alternatively, the proximal anchor 104 includes a one-way passage that allows the tether 106 to pass through proximally to increase the device curvature, and then holds the device shape by preventing the tether 106 from passing distally through the proximal anchor 104 to loosen tension and reduce the device's curvature.

In some embodiments, the curvature device 100 is formed so as to be moveable between a collapsed/crimped configuration (having a low profile) to the expanded configuration shown in FIGS. 2A and 2B. For example, the curvature device 100 may be formed at least partly from a self-expanding shape memory material such as nitinol. In alternative embodiments, the curvature device 100 may be formed as a balloon-like structure expandable and collapsible by directing or withdrawing fluid from the structure, respectively.

In some embodiments, the curvature device 100 may be curved by pushing the proximal anchor 104 toward the distal anchor 102, in addition to or as an alternative to pulling the distal anchor 102 toward the proximal anchor 104. For example, this may be accomplished using the proximal end of a delivery catheter and/or using a pushing rod or other structure that may be routed through the delivery catheter to the deployment site.

In some embodiments, the curvature device 100 is formed at least partly from one or more bioresorbable materials. In such embodiments, the device may be left in place within the CS and GCV post procedure to be resorbed by the patient. In some embodiments, the curvature device may have a stent-like structure or other lumen containing structure that allows blood flow through the device after implantation. In some embodiments, at least a portion of the device is formed of a non-bioresorbable material (e.g., nitinol), which may be removed after carrying out the corresponding procedure or which may be left behind as a long-term or permanent implant.

One or both anchors 102, 104 may be formed as sections having diameters sufficient to, when expanded, fill the space of the targeted vasculature anatomy and firmly abut against the inner wall of the CS and/or GCV (e.g., about 2.5 to 5 mm, or about 3 to 4.5 mm for a typical adult). In some embodiments, the anchors 102, 104 may include barbs, tines, or other similar structures for enhancing grip of the anchors into the inner wall of the vasculature, though in preferred embodiments, the anchors omit such barbs, tines, or hooks, and are configured for temporary placement so that the device can be retrieved after the associated procedure (e.g., after an associated valve leaflet grasping and/or clip placement procedure). Although the illustrated embodiment is shown as including two separate anchors, alternative embodiments may include one or more centrally disposed anchors for further securing the device within the targeted vasculature. The total length of the curvature device 100 can vary according to patient anatomy and/or procedural requirements. In a typical implementation, a curvature device may have a length of about 30 mm to about 100 mm.

The illustrated embodiment has a shape with a body 103 that is, at least in some portions, narrower than the anchors 102 and 104, enabling the anchors 102 and 104 to provide the anchoring functionality while the body 103 functions to provide structural integrity between the anchors 102 and 104. Additionally, or alternatively, the curvature device 100 may be configured such that substantially all of the length of the device expands to abut against the inner walls of the targeted vasculature. Accordingly, the proximal and distal anchors 102, 104 are not to be considered as the only sections of the device capable of or intended to function as anchoring mechanisms.

In some embodiments, the anchors 102 and 104 are formed as expandable ring structures, and the body 103 is formed as one or more wires and/or mesh structures extending between the anchors to provide sufficient structural integrity to the curvature device 100. For example, the anchors 102, 104 and/or the body 103 may be formed at least partially from a shape-memory material, such as nitinol. In some embodiments, the curvature device 100 may be formed at least partially as a balloon-like structure capable of being selectively inflated and deflated to move the device between the expanded/deployed and retracted/collapsed configuration. The balloon-structure of the curvature device may, for example, be at least partially formed from any biocompatible polymer known in the art that is capable of sufficient expansion to move between an expanded/deployed and retracted/collapsed position.

In some embodiments, the curvature device 100 is configured to deploy in a state of enhanced curvature (such as shown in FIG. 2B) without requiring an additional curving action or tether tightening action. For example, rather than being deployed in a configuration of relatively lower curvature, (such as is shown in FIG. 2A), the curvature device 100 may be configured to deploy with the relatively greater curvature intended to reduce the annulus and/or bring the leaflets closer to one another. In some embodiments, the curvature device 100 includes sufficient structural integrity to, once deployed, provide and maintain sufficient curvature without the need to tension the device using the tether 106, and the tether 106 may therefore be omitted. As explained in more detail below, the curvature device 100 may be deployed and retracted by selectively sheathing and unsheathing the device, respectively.

Some curvature device embodiments are configured to be retrievable. For example, in a typical implementation, the curvature device 100 is deployed in the targeted GCV and CS and is used to enhance the curvature of the associated anatomy to reduce the mitral valve annulus and/or bring the mitral valve leaflets closer to one another. An associated mitral valve procedure may then be concurrently performed while the deployed curvature device is used to better position the valve anatomy. When the associated mitral valve procedure is completed, the curvature device 100 is retrieved and removed from the patient's vasculature. As shown, the anchors 102 and 104 include tapered sections 120 to aid in retraction of the curvature device 100 to enable removal of the device. In preferred embodiments, at least the proximal anchor 104 includes a tapered section 120 that tapers to a smaller diameter in the proximal direction. With this structure, the curvature device 100 may more easily be retrieved. For example, a sheath may more easily be repositioned over the proximal anchor 104 and then the remainder of the curvature device 100.

In alternative embodiments, the curvature device 100 may remain in the patient as a permanent implant. For example, the curvature device 100 may omit the tether 106, or the tether 106 may be removed after tightening the device, leaving the remainder of the curvature device 100 implanted within the patient.

Figure 3:
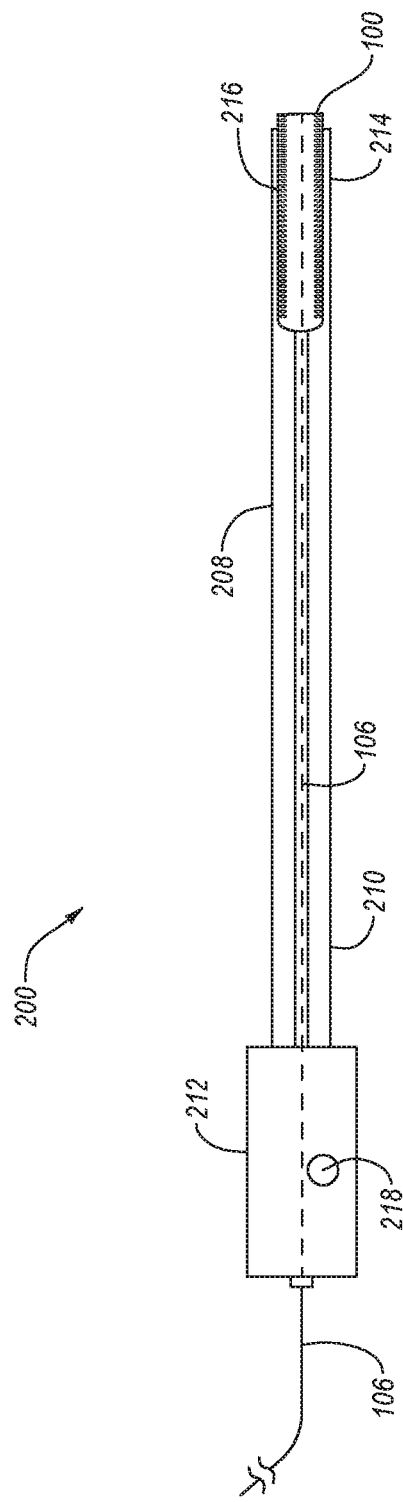
FIG. 3 illustrates an exemplary delivery system that may be utilized to delivery and deploy the curvature device of FIGS. 2A and 2B.

FIG. 3 illustrates an exemplary delivery system 200 which may be utilized to deliver the curvature device 100 to the targeted CS and GCV. In the illustrated embodiment, the delivery system 200 includes a catheter 208 extending from a proximal end 210, where it is coupled to a handle 212, to a distal end 214. At the distal end 214, a sheath 216 is positioned around the curvature device 100 to hold the curvature device 100 in a collapsed configuration. As shown, the tether 106 passes from the curvature device 100 through an inner lumen of the catheter 208 and to the handle 212.

The handle 212 may include one or more controls, such as illustrated control 218, for providing a user the ability to control one or more mechanisms of the delivery system 200. In the illustrated embodiment, the control 218 is operatively connected to the tether 106, such that actuation of the control 218 adjusts tensioning of the tether 106. The control 218 may be configured as a dial, switch, slider, lever, button, or other control. Other controls (not shown) operatively connected to other components of the system may be similarly configured. For example, the delivery system 200 may include one or more controls operatively coupled to a corresponding control line extending to the distal end 214 of the catheter 208, the control enabling adjustment to the tension of the corresponding control line to provide bending and steering of the distal end 214 of the catheter 208.

In some embodiments, the handle 212 also includes a tension meter operatively connected to the tether 106 to provide an indication of the current tension of the tether 106.

During deployment, the sheath 216 may be proximally retracted relative to the curvature device 100 so that the curvature device 100 may deploy from the sheath 216. Additionally, or alternatively, the curvature device 100 may be distally pushed relative to the sheath 216 (e.g., using a push rod or other deployment structure extending through the inner lumen of the catheter 208 to the curvature device 100).

In one exemplary deployment procedure, the delivery system 200 delivers the curvature device 100 to the CS and GCV using a minimally invasive transfemoral or transjugular approach, by which the distal end 214 of the catheter 208 is routed to the right atrium of the heart, then into the CS, and then further so that it extends partially into the GCV. In some circumstances, a transjugular approach is preferred so that the concurrent heart valve repair procedure (e.g., interventional clip placement) is free to use the transfemoral approach. In some circumstances, both the right and left femoral veins may be utilized (e.g., one for delivery of the curvature device and the other for the concurrent clip delivery or other heart valve procedure). In alternative embodiments, other approaches, such as a transapical approach, may be used.

Figure 4A:
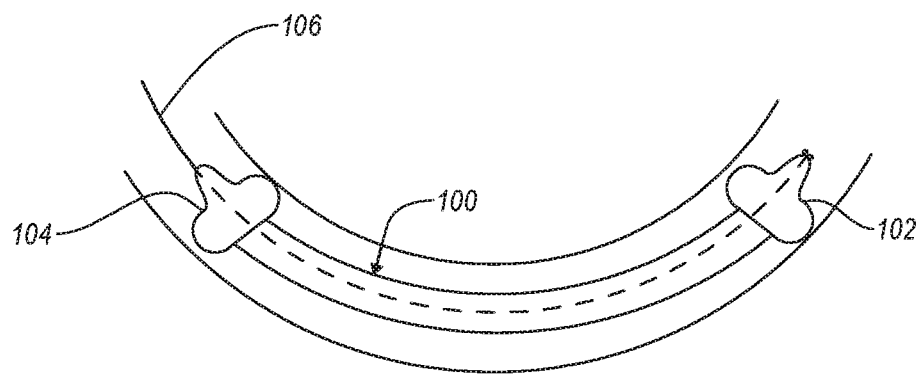
FIGS. 4A and 4B illustrate the curvature device of FIGS. 2A and 2B in a deployed state within the GCV and CS of the heart.
Figure 4B:
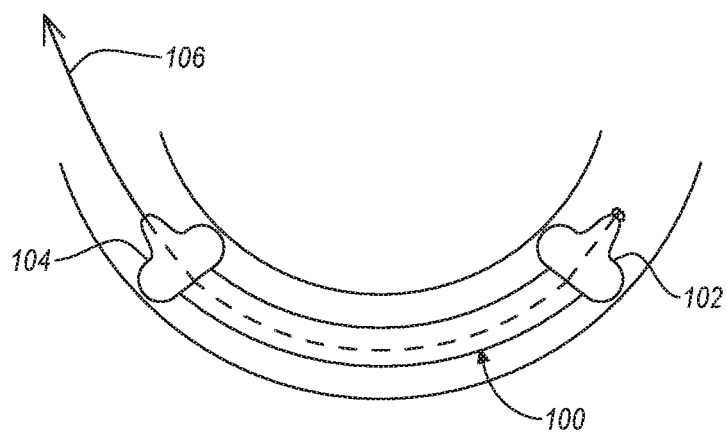

FIGS. 4A and 4B illustrate the curvature device 100 deployed within the GCV and CS. FIG. 4B illustrates an increase in curvature of the device 100 relative to the curvature of FIG. 4A as a result of an increase in tension applied to the tether. In a preferred deployment operation, the sheath 216 is retracted (and/or the curvature device 100 is pushed) so that the distal anchor 102 of the curvature device 100 may expand/deploy and lodge in the GCV. Further retraction of the sheath 216 (and/or further pushing of the curvature device 100) allows the proximal anchor 104 to expand/deploy and lodge in the CS. The application of tension to the tether 106 pulls the curvature device 100 into a position of relatively greater curvature. As shown, the increased curvature of the curvature device 100 causes the adjacent sections of the CS and the GCV to further curve as well. This structural change to the heart anatomy causes the posterior leaflet to move closer to the anterior leaflet and/or tends to constrain the mitral valve annulus in a relatively more reduced position.

The curvature device 100 may remain in the deployed and curved configuration during the course of a concurrent valve repair procedure, such as the implantation of an interventional clip device to treat regurgitation of the mitral valve. Advantageously, deployment of the curvature device 100 places the valve leaflets in a more favorable position that enables more effective grasping of the valve leaflets. More effective grasping of the leaflets leads to more effective positioning of the interventional clip device(s) and therefore better treatment of the underlying regurgitation pathology.

After the concurrent valve repair procedure is completed, the curvature device 100 may be removed from the patient's vasculature. In one exemplary removal process, the tether 106 is manipulated to release tension in the device 100 and reduce the curvature of the device 100. The device 100 may then be repositioned within the catheter 208 by moving the sheath 216 distally forward over the curvature device 100 and/or by proximally retracting the curvature device 100 into the sheath 216. Positioning the curvature device 100 back into the catheter 208 can cause the curvature device 100 to move from the expanded configuration back into a collapsed configuration. The delivery system 200 is then withdrawn from the patient's vasculature.

In one embodiment, a method for using a curvature device to enhance the effectiveness of a mitral valve repair procedure includes one or more of the following steps: (1) routing a guidewire into the CS and GCV (e.g., via a transfemoral or transjugular approach); (2) advancing a delivery catheter over the guidewire until the distal end of the catheter passes into the CS and reaches partially into the GCV; (3) proximally retracting a sheath of the delivery catheter relative to the housed curvature device to release and anchor a distal section of the curvature device in the GCV; (4) further proximally retracting the sheath relative to the curvature device to release and anchor a proximal section of the curvature device in the CS; (5) applying tension to a tether extending at least partially through the curvature device to increase the curvature of the device, the increased curvature of the deployed curvature device thereby increasing the curvature of the portions of the GCV and CS in which the device is positioned; (6) performing the mitral valve repair procedure (e.g., an interventional leaflet clip placement procedure); (7) releasing tension in the curvature device; (8) distally advancing the sheath relative to the curvature device to rehouse the curvature device; and (9) withdrawing the delivery catheter and the guidewire.

In some embodiments, the curvature device increases in curvature to adjust the curvature of the GCV and CS, relative to the curvature of the anatomy prior to deployment and tensioning of the curvature device, by about 5%, 10%, 20%, 30%, 40%, or 50%, or increases the curvature by a percentage within a range defined by any two of the foregoing values.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to the illustrated curvature device 100 or delivery system 200 may be combined with any element described in relation to any of the alternative embodiments described herein.

What is claimed is:

1. An interventional system for temporarily adjusting the structure of a heart, the system comprising:
   a curvature device moveable between a collapsed configuration and an expanded configuration, the curvature device including:
      a distal end section with a distal end configured to abut an inner wall of a body lumen when deployed to the expanded position;
      a proximal end section with a proximal end configured to abut the inner wall of the body lumen remote from the distal end in a longitudinal direction when deployed to the expanded position;
      an intermediate section extending between the distal end section and the proximal end section with a cross-sectional dimension in a direction transverse to the longitudinal direction less than a cross-section dimension of at least one of the distal end section and the proximal end section, the proximal end section comprising a first portion and an enlarged second portion, the first portion tapering away from the enlarged second portion that is disposed closer to the intermediate section than the first portion, the first portion has a cross-sectional dimension less than the cross- sectional dimension of the intermediate section; and
   a tether disposed at the distal end section and extending through the intermediate section and past the proximal end section, the tether being tensionable such that an increase in tension increases the curvature of the device, and a release of tension lessens the curvature of the device.

2. The interventional system of claim 1, wherein the curvature device is at least partially formed from a shape memory material that enables the device to self-expand to the expanded configuration when not constrained to the collapsed configuration.

3. The interventional system of claim 1, wherein the curvature device is at least partially formed as a balloon structure capable of being filled with a fluid to move toward the expanded configuration and withdrawn of fluid to move toward the collapsed configuration.

4. The interventional system of claim 1, wherein the proximal end section includes an anchoring structure having an aperture through which the tether passes.

5. The interventional system of claim 1, wherein the curvature device is formed at least partially from one or more bioresorbable materials.

6. The interventional system of claim 1, wherein the curvature device is formed so as to have one or more lumens when in the expanded configuration so as to allow the passage of blood through the one or more lumens.

7. The interventional system of claim 1, wherein at least a portion of the distal end section and proximal end section include tines for enhancing grip of targeted vasculature when the curvature device is deployed at the targeted vasculature.

8. The interventional system of claim 1, further comprising a delivery system, the delivery system including:
   a delivery catheter having a sheath configured to house the curvature device to maintain the curvature device in the collapsed configuration while housed within the sheath; and
   a handle coupled to the delivery catheter, the tether extending to the handle, the handle including a tether control operatively coupled to the tether to enable adjusting of tension in the tether through actuation of the control.

9. The interventional system of claim 8, the delivery system further comprising one or more control lines extending from the handle to the delivery catheter such that tensioning of the one or more control lines acts to bend the delivery catheter to provide steering functionality to the delivery catheter.

10. The interventional system of claim 8, wherein the sheath is proximally retractable relative to the housed curvature device.

11. A method for temporarily adjusting the structure of a body lumen, the method comprising:
   delivering a curvature device to a first location within a body lumen;

deploying the curvature device such that a distal end section of the curvature device abuts an inner wall of the body lumen and such that a proximal end section of the curvature device abuts the inner wall of the body lumen remote from the distal end section, an intermediate section of the curvature device extending between the distal end section and the proximal end section with a cross-sectional dimension in a direction transverse to a longitudinal axis of the curvature device being less than a cross-section dimension of at least one of the distal end section and the proximal end section, the proximal end section comprising a first portion and an enlarged second portion, the first portion tapering away from the enlarged second portion that is disposed closer to the intermediate section than the first portion, the first portion has a cross-sectional dimension less than the cross-sectional dimension of the intermediate section; and tensioning a tether of the curvature device, the tether being coupled to the distal end section and passing through the intermediate section and the proximal end section such that the tensioning causes the distal end section to bend toward the proximal end section to increase the curvature of the curvature device.

12. The method of claim 11, wherein the curvature device is delivered to the body lumen by first routing a guidewire to the body lumen, and subsequently routing a delivery system housing the curvature device along the guidewire.

13. The method of claim 11, wherein the curvature device is delivered to the body lumen, the delivery system including:
  a delivery catheter having a sheath configured to house the curvature device to maintain the curvature device in the collapsed configuration while housed within the sheath; and
  a handle coupled to the delivery catheter, the tether extending to the handle, the handle including a tether control operatively coupled to the tether to enable adjusting of tension in the tether through actuation of the control.

14. The method of claim 11, wherein the curvature device is delivered using a transjugular approach or a transfemoral approach.

15. The method of claim 11, wherein the curvature device is at least partially formed from a shape memory material that enables the device to self-expand to the expanded configuration when not constrained to the collapsed configuration.

16. The method of claim 11, further comprising releasing tension in the tether to lessen the curvature of the curvature device, and removing the curvature device from the body lumen.

17. An interventional system for temporarily adjusting the structure of a body lumen, the system comprising:
  a curvature device moveable between a collapsed configuration having a profile suitable for delivery of the device to a body lumen of a patient and an expanded configuration having a profile suitable for abutting an inner wall of the body lumen, the curvature device including:
    a distal end section with a distal end configured to abut an inner wall of a body lumen when deployed to the expanded position;
    a proximal end section with a proximal end configured to abut the inner wall of the body lumen when deployed to the expanded position; and
    an intermediate portion disposed between the distal end section and the proximal end section,
  wherein the curvature device has a curvature such that when deployed to the expanded configuration the curvature device is configured to abut against the body lumen to increase anatomical curvature of the body lumen,
  wherein, each of the proximal end section and the distal end section comprise a first tapered portion and a second enlarged portion, the first tapered portion of the proximal end section tapering away from the second enlarged portion that is disposed closer to the intermediate portion than the second enlarged portion, the second enlarged portion having a cross-sectional dimension transverse to a longitudinal axis of the curvature device that is greater than a cross-sectional dimension of the intermediate portion, the first tapered portion encircling the longitudinal axis of the curvature device and the first tapered portion having a symmetrical cross-section about the longitudinal axis.

* * * * *